United States Patent [19]
Bittner et al.

[11] Patent Number: 5,878,938
[45] Date of Patent: Mar. 9, 1999

[54] SURGICAL STAPLER WITH IMPROVED LOCKING MECHANISM

[75] Inventors: John R. Bittner, Loveland; William G. Bowser, Cincinaati; Joseph C. Hueil, Loveland; David H. Ruder, Mason, all of Ohio

[73] Assignee: Ethicon Endo-Surgery, Inc., Cincinnati, Ohio

[21] Appl. No.: 909,037

[22] Filed: Aug. 11, 1997

[51] Int. Cl.$^6$ ............................................. A61B 17/04
[52] U.S. Cl. ............................................. 227/175.4
[58] Field of Search ..................... 227/19, 175.1, 227/175.2, 175.4, 176.1, 175.3

[56] References Cited

U.S. PATENT DOCUMENTS

| | | | |
|---|---|---|---|
| 4,892,244 | 1/1990 | Fox et al. . | |
| 4,955,959 | 9/1990 | Tompkins . | |
| 5,129,570 | 7/1992 | Schulze et al. . | |
| 5,485,947 | 1/1996 | Olson et al. . | |
| 5,584,425 | 12/1996 | Savage et al. . | |
| 5,669,544 | 9/1997 | Schulze et al. | 227/19 |
| 5,673,840 | 10/1997 | Schulze et al. | 227/19 |
| 5,673,841 | 10/1997 | Schulze et al. | 227/19 |
| 5,673,842 | 10/1997 | Bittner et al. | 227/175.4 |
| 5,680,983 | 10/1997 | Plyley et al. | 227/19 |
| 5,692,668 | 12/1997 | Schulze et al. | 227/19 |
| 5,797,538 | 8/1998 | Heaton et al. | 227/19 |

*Primary Examiner*—John Sipos

[57] ABSTRACT

A surgical stapler for effecting simultaneous cutting and stapling of tissue includes a frame and a staple cartridge positionable in the frame. The stapler includes a knife blade mounted for movement distally of the staple cartridge, the knife blade having a retraction lock feature including a locking portion for abutment to a roof member of a spacer carried on the frame in a locked position, to prevent movement of the knife blade, unless the stapler is fitted with a fresh, unused staple cartridge. The locking portion is spring loaded by a leaf spring into the locked position. The knife blade includes a spring notch which coacts with the leaf spring to mechanically lift and pivotally thrust the knife blade to the locked position when the knife blade is retracted after use. The lift or thrust feature clears out tissue accumulation which enhances the ability of the knife to restore to its full elevated return position.

16 Claims, 7 Drawing Sheets

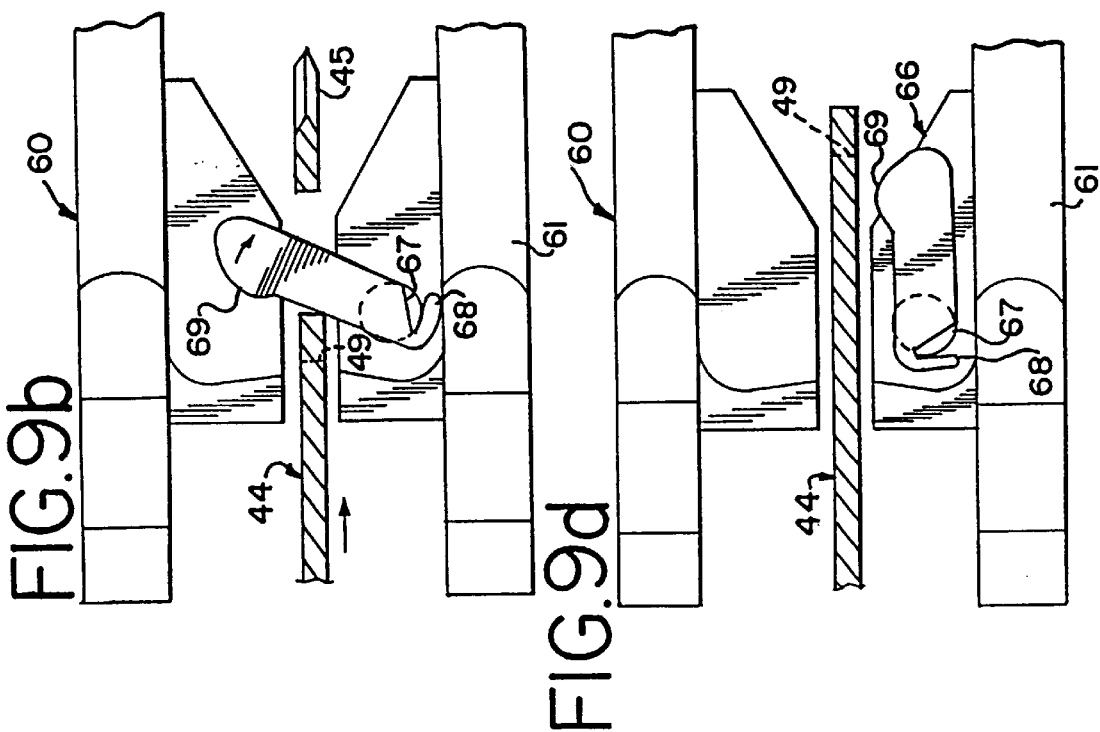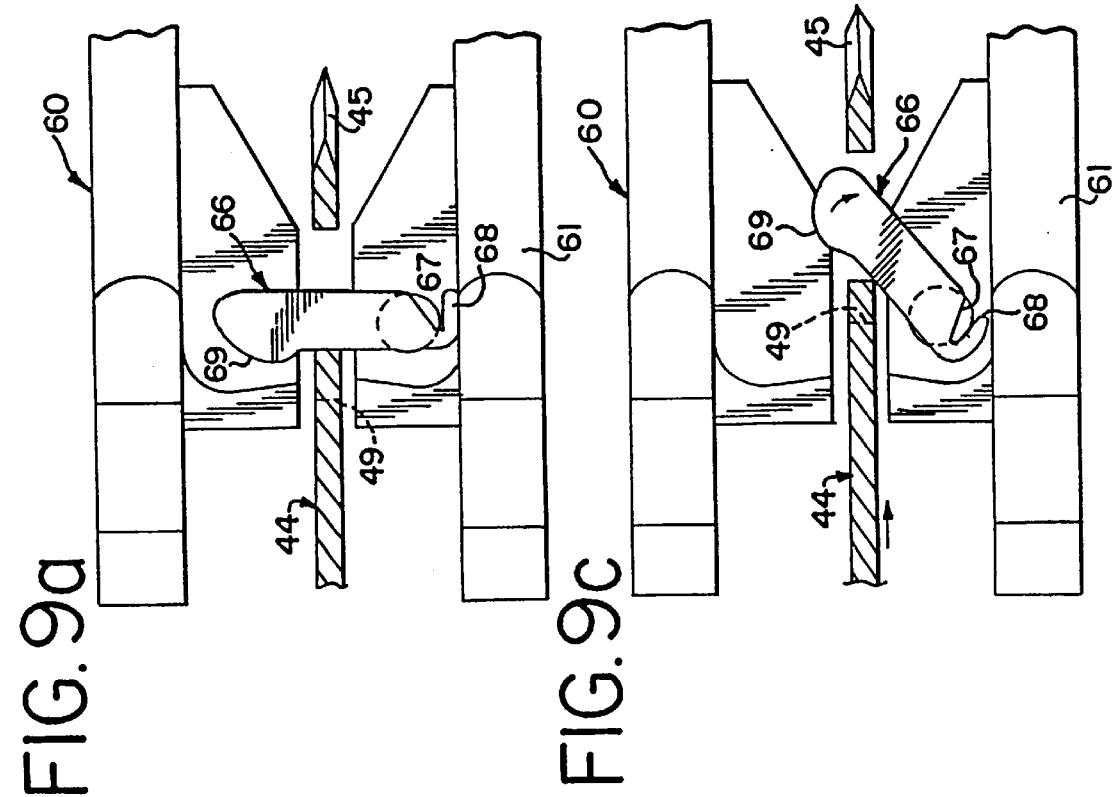

SURGICAL STAPLER WITH IMPROVED LOCKING MECHANISM

TECHNICAL FIELD

The present invention relates generally to a surgical stapler that prevents reuse of a previously used staple cartridge, and more particularly to a surgical stapler having a locking mechanism that prevents such reuse, while minimizing the force required for actuating the stapler.

BACKGROUND OF THE INVENTION

U.S. Pat. No. 5,129,570, hereby incorporated by reference, discloses a surgical stapler configured for applying rows of staples in lieu of suturing tissue. This type of surgical device greatly facilitates surgical procedures, and desirably reduces the time otherwise required for suturing tissue.

The surgical stapler disclosed in the above-referenced patent is configured to employ a removable staple cartridge, which typically includes a plurality of rows of staples. Attendant to each use of the surgical stapler, a fresh, unused staple cartridge is inserted into a frame of the stapler, with the device then positioned for use for suturing tissue. The stapler includes one or more firing wedges which can be advanced through the staple cartridge, and which cooperate in a cam-like manner with drivers within the cartridge to fire the staples, driving them through tissue and against an associated anvil of the stapler for closing the staples. For reuse, the firing wedges are retracted, the used staple cartridge removed, and an unused staple cartridge inserted into the device.

While some staplers are configured to perform the sole function of stapling, one particularly useful configuration of a surgical stapler effects simultaneous cutting and stapling (i.e., suturing) of tissue. Such devices, sometimes referred to as linear cutters, include a knife blade which is advanced together with the firing wedges of the surgical stapler during use. In this manner, cutting of tissue is effected simultaneously with stapling, greatly facilitating efficiency in surgical procedures.

In order to preclude inadvertent use of a stapler with a used staple cartridge, thereby avoiding inadvertent cutting of tissue without simultaneous application of staples, surgical staplers are ordinarily provided with locking mechanisms which prevent actuation of the device unless fitted with a fresh, unused staple cartridge. U.S. Pat. No. Re. 34,519, to Fox et al., hereby incorporated by reference, discloses various embodiments of such locking mechanisms, with the above-referenced U.S. Pat. No. 5,129,570 disclosing further embodiments of such locking mechanisms.

In the locking mechanisms disclosed in U.S. Pat. No. 5,129,570, the knife blade of the illustrated surgical stapler is configured to cooperate with a member provided on an unused staple cartridge for permitting advancement of the knife blade, and actuation of the stapler, when fitted with the unused cartridge. In particular, the knife blade is mounted for limited vertical movement in opposition to a biasing spring, which spring ordinarily urges the knife blade into a locked position in association with a roof member of the stapler. Insertion of an unused staple cartridge into the device acts to displace the knife blade, in opposition to the biasing spring, into alignment with a slot defined by the roof member. This permits advancement of the knife blade and the associated firing wedges of the stapler, thus permitting simultaneous cutting and stapling of tissue. During advancement of the knife blade, the cooperating member on the staple cartridge is displaced. As a consequence, upon retraction of the knife blade and firing wedges, the knife blade is urged by the biasing spring into engagement with the roof member and out of alignment with the slot therein, thus preventing reuse of the device until fitted with an unused staple cartridge.

In particular, current commercial embodiments of surgical staplers in accordance with the above-referenced patent include a rotatable member mounted on the staple cartridge for cooperation with the associated knife blade. This rotatable member (sometimes referred to as a swing tab) is configured to interferringly engage the body of the staple cartridge as the member is rotated by the knife blade, thus providing a snap-over like action to maintain the rotatable member in an out-of-the-way disposition. This prevents the knife blade from engaging the rotatable member and returning to its original position as the blade is retracted.

In U.S. application Ser. No. 08/611,161 filed Mar. 5, 1996 by the same inventor as the present application, a surgical stapler includes a staple cartridge having a rotatable member which is initially positioned to coact with a knife blade of the surgical stapler to position the knife blade for distal movement in the device, thus permitting actuation for simultaneous cutting and stapling of tissue. Notably, the rotatable member is specifically configured to move to an out-of-the-way position during actuation of the device without application of undue force to the rotatable member. Convenient and efficient use is facilitated by the resultant reduction in "force to fire" of the stapler.

The surgical stapler disclosed in the aforementioned application includes a frame, and a staple cartridge positionable in the frame. The staple cartridge comprises a cartridge body containing at least one row of staples, with the cartridge defining an elongated knife slot. At least one firing wedge is carried by the frame of the surgical stapler for movement longitudinally of the stapler. Such longitudinal movement, distally of the stapler, effects sequential driving of the staples from the staple cartridge through tissue and against an associated anvil of the stapler.

A knife blade travels across a spacer which is mounted into the frame of the stapler for movement through the elongated knife slot defined by the staple cartridge. The knife blade is also vertically movable between a first, locked position wherein the knife blade is substantially prevented from moving through the knife slot, and a second, unlocked position wherein the knife blade is movable through the slot in the staple cartridge.

The staple cartridge includes a rotatable member which is movable from a first position to a second position. In its first position, the rotatable member is engagable with the knife blade as the staple cartridge is positioned in the frame of the stapler. This engagement acts to move the knife blade from its first, locked position to its second, unlocked position.

During actuation of the stapler, the rotatable member on the cartridge is moved to the second position thereof by the knife blade as the knife blade is advanced in forward or distal direction through the knife slot. Simultaneous cutting and stapling of tissue is effected during distal advancement of the knife blade.

The rotatable member on the staple cartridge includes a resiliently flexible portion which is yieldably engagable with the body of the staple cartridge as the rotatable member is moved from its first position to its second position. After such movement, the flexible portion on the rotatable member is engagable with the cartridge body to maintain the rotatable member in the second position thereof. Upon retraction of the knife blade, the blade returns to its first, locked position wherein it is substantially prevented from movement through the knife slot (i.e., its position prior to insertion of an unused staple cartridge). This takes place since the rotatable member on the staple cartridge has been moved to its second position, and thus is no longer engagable with the knife blade. Reuse of the stapler is effected by removal of the spent cartridge, and insertion of a fresh, unused staple-filled cartridge.

A first end portion of the rotatable member is pivotally mounted on the cartridge body of the staple cartridge. The resiliently flexible portion of the member comprises a cantilevered arm at this first end portion, which arm is engagable with the cartridge body as the rotatable member is moved from its first to its second position. Additionally, the rotatable member includes a cam projection engagable by the knife blade of the stapler as the knife blade is advanced distally through the knife slot. The cam projection facilitates movement of the rotatable member to the second position thereof. The cam projection is provided generally at a second end portion of the rotatable member, spaced from the first end portion thereof.

The device described provides an effective arrangement for preventing inadvertent use of the surgical stapler with a used staple cartridge. It is, however, possible that a build up or accumulation of tissue around the locking mechanism could inhibit the knife blade from efficiently seating against the roof member in the retracted condition.

Additionally, the retraction of the knife during multiple return strokes may cause a portion of the knife blade to embed into the roof member of the locking mechanism. This embedding, plus the tissue buildup can possibly cause an occasional inhibition of the knife to be efficiently restored to its full upright position, locked behind the roof member.

SUMMARY OF THE INVENTION

The present invention contemplates an improved knife blade and biasing spring arrangement having a spring stop surface arranged in a side of the blade facing the biasing spring. The knife blade is reciprocally mounted within a frame. The knife blade travels on a spacer which provides a stationary abutment. The stop surface interacts with the spring to cause an upward thrust motion to the knife during return stroke to assure efficient knife blade relocking, to be unlocked by a mechanism associated with the installation of an unused staple cartridge. The interaction of the biasing spring and the spring stop surface also causes a forced mechanical upward pivoting of the knife on the return stroke. This allows a locking portion of the knife blade to abut a portion of the stationary abutment, preventing reciprocation of the knife blade in a forward direction. The pivoting motion also causes a linear deceleration which avoids embedment of an upstanding portion of the blade (i.e., the swing tab activation projection), into the stationary abutment on the return stroke of the knife blade.

The preferred embodiment of the invention contemplates a surgical stapler comprising a frame including upper and lower frame pieces and a spacer. A leaf spring is carried by the spacer, the leaf spring having a spring finger. A staple cartridge is positionable in the frame and includes a cartridge body containing at least one row of staples, the cartridge defining an elongated knife slot. At least one firing wedge is carried by the frame for movement along a spacer mounted into the frame longitudinally of the staple cartridge for effecting sequential driving of the staples from the cartridge. A knife blade is also carried by the frame for movement longitudinally of the staple cartridge through the elongated knife slot, the knife blade being movable between a first position wherein the knife blade is substantially prevented from moving through the knife slot, and a second position wherein the knife blade is movable through the knife slot. The leaf spring is arranged to urge the knife blade toward the first position, the knife blade having a spring stop surface formed on a first side of the knife blade facing the leaf spring. The stop surface faces toward a retraction direction of the knife blade. The spring finger is inclined from the spacer toward the knife blade and pivotable at the spacer, the spring finger having a free end engagable by the stop surface. The spring finger is pivoted by retraction of the blade, with the blade elevated by pivoting of the spring finger.

The preferred embodiment is further described as having a spring notch formed or cut into the knife blade, and the stop surface is formed as a transverse surface of the spring notch. The spring notch further includes an oblique surface contiguous to the stop surface and forming a corner therewith. Additionally, the spacer can include a stationary stop surface facing in a retraction direction and adjacent to the knife blade. The knife blade includes a locking portion facing away from the retraction direction and arranged to abut the stationary stop surface in the first position. The locking portion includes a forward facing surface of a recess formed or cut into a second side of said knife blade opposite the first side.

The spacer can include a stationary block having a knife slot therethrough for allowing sliding reciprocation of the knife blade and having a roof portion overlying the knife blade within the knife slot. The stationary stop surface is located on a rear surface of the roof portion.

Other features and advantages of the present invention will become readily apparent from the following detailed description, the accompanying drawings, and the appended claims.

BRIEF DESCRIPTION OF THE DRAWINGS

FIGS. 9a to 9d are fragmentary, bottom plan views illustrating the rotatable member of the locking mechanism as it is moved from a first to a second position thereof by the associated cutting knife blade of the surgical stapler.

DETAILED DESCRIPTION

Figure 1:
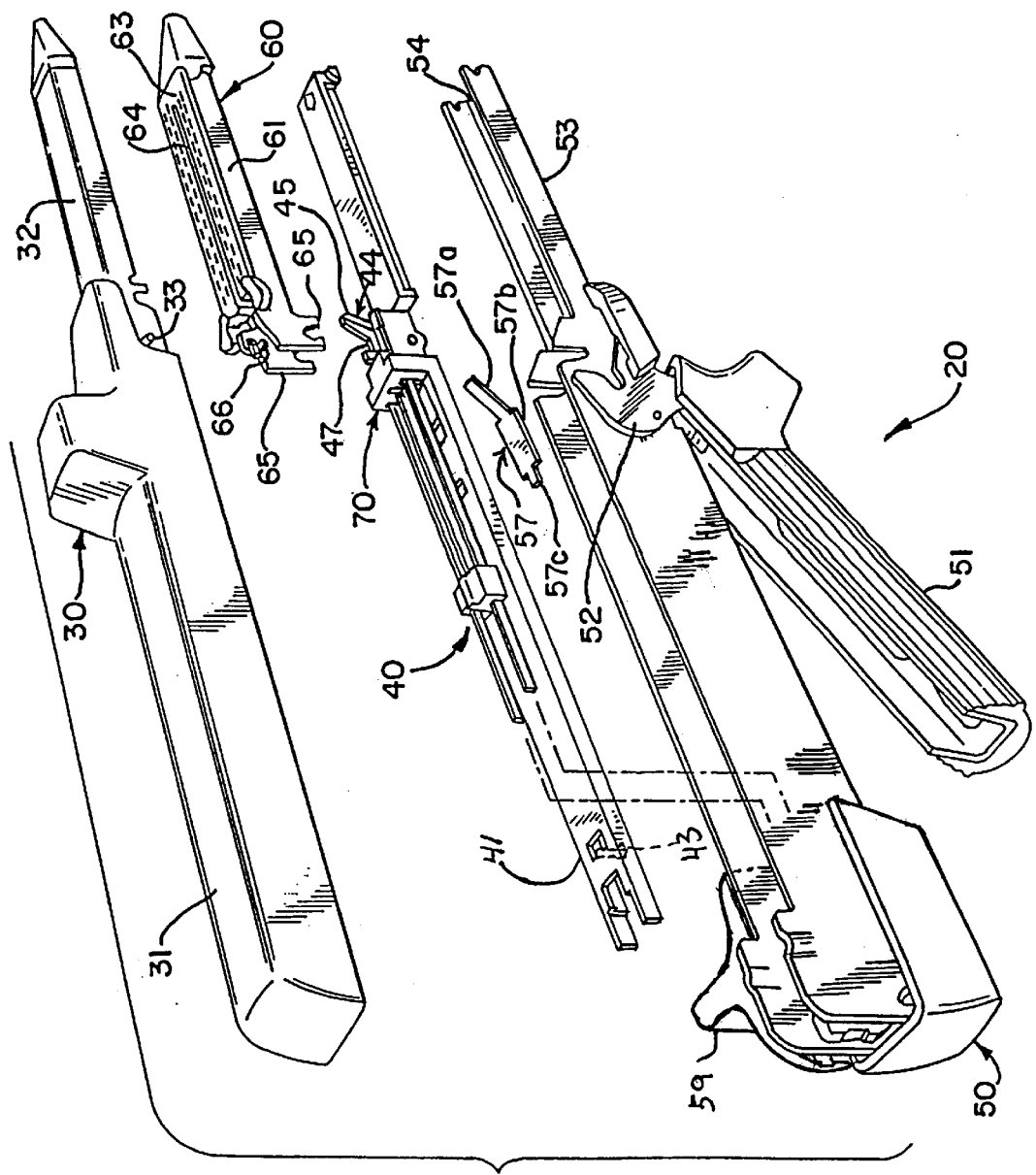
FIG. 1 is an exploded perspective view of a surgical stapler embodying the principles of the present invention.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

Figure 8:
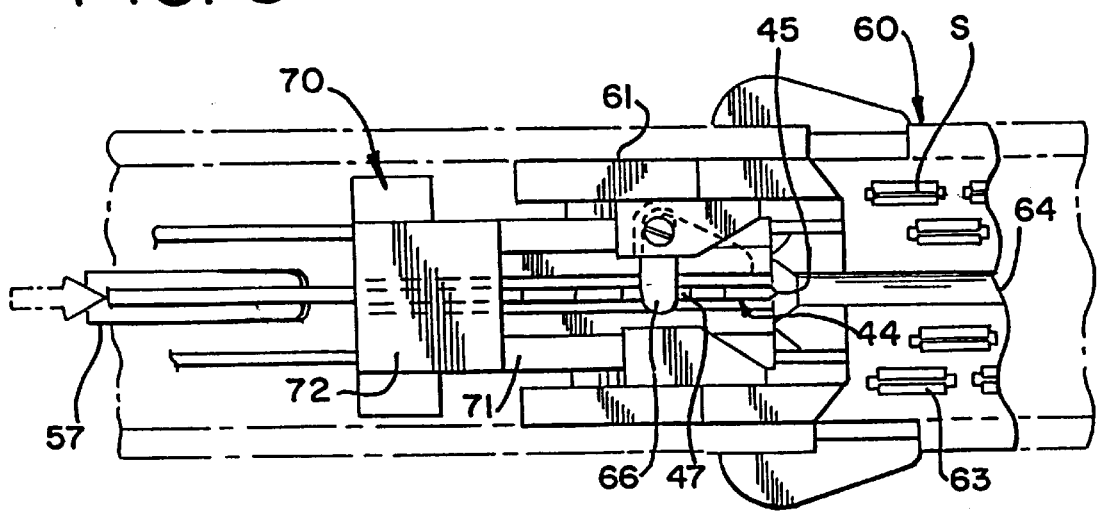
FIG. 8 is a fragmentary top plan view taken along line 8—8 of FIG. 6 showing the knife blade prior to actuation of the stapler.

As illustrated in FIG. 1, a surgical stapler 20 embodying the principles of the present invention comprises an upper frame piece 30, a firing or pusher assembly 40, a spacer 41, a lower frame piece 50, and a removable staple cartridge 60. Upper and lower frame pieces 30 and 50 and the spacer 41 collectively provide a frame of the stapler, with the firing assembly 40 carried by the spacer 41 for movement longitudinally of the staple cartridge for effecting sequential driving of staples S (FIG. 8) from the cartridge. The spacer 41 is locked into the lower frame piece 50 by a pin 58 at a front end of the frame piece 50 (see FIG. 2) and a downwardly and frontwardly extending hook 43 at a rear end of the frame piece 50.

The staple cartridge 60 fits within lower frame piece 50. Specifically, the front part of the staple cartridge 60 fits into a lower jaw 53 defining a channel 54, with the parallel side walls of the cartridge body 61 of the staple cartridge 60 fitted within the lower jaw channel 54. The back or proximal portion of the staple cartridge 60 has a rotatable member 66, which initially extends in a first position generally transversely of the staple cartridge. As will be further described, the rotatable member 66 is engagable with a knife blade 44 of the firing assembly 40. Attendant to disposition of the staple cartridge in the lower frame piece of the stapler, two legs 65 of the staple cartridge secure the cartridge to the lower frame piece 50. These legs 65 engage the cylindrical pin 58 of lower frame piece 50, as illustrated in exploded perspective view in FIG. 2.

As illustrated in FIG. 1, the upper frame piece 30 has a rear upper handle portion 31 and a front upper jaw portion 32 which defines an anvil against which the staples in cartridge 60 are driven. The lower frame piece 50 includes a pivotable lower handle portion 51 positioned rearwardly of the lower jaw portion 53. In the illustrated embodiment, the longitudinally movable firing assembly 40, a biasing leaf spring 57, and the staple cartridge 60 are fitted onto spacer 41 in the lower frame piece 50. It is within the purview of the present invention to otherwise position these components in either one of the upper and lower frame pieces.

Figure 2:
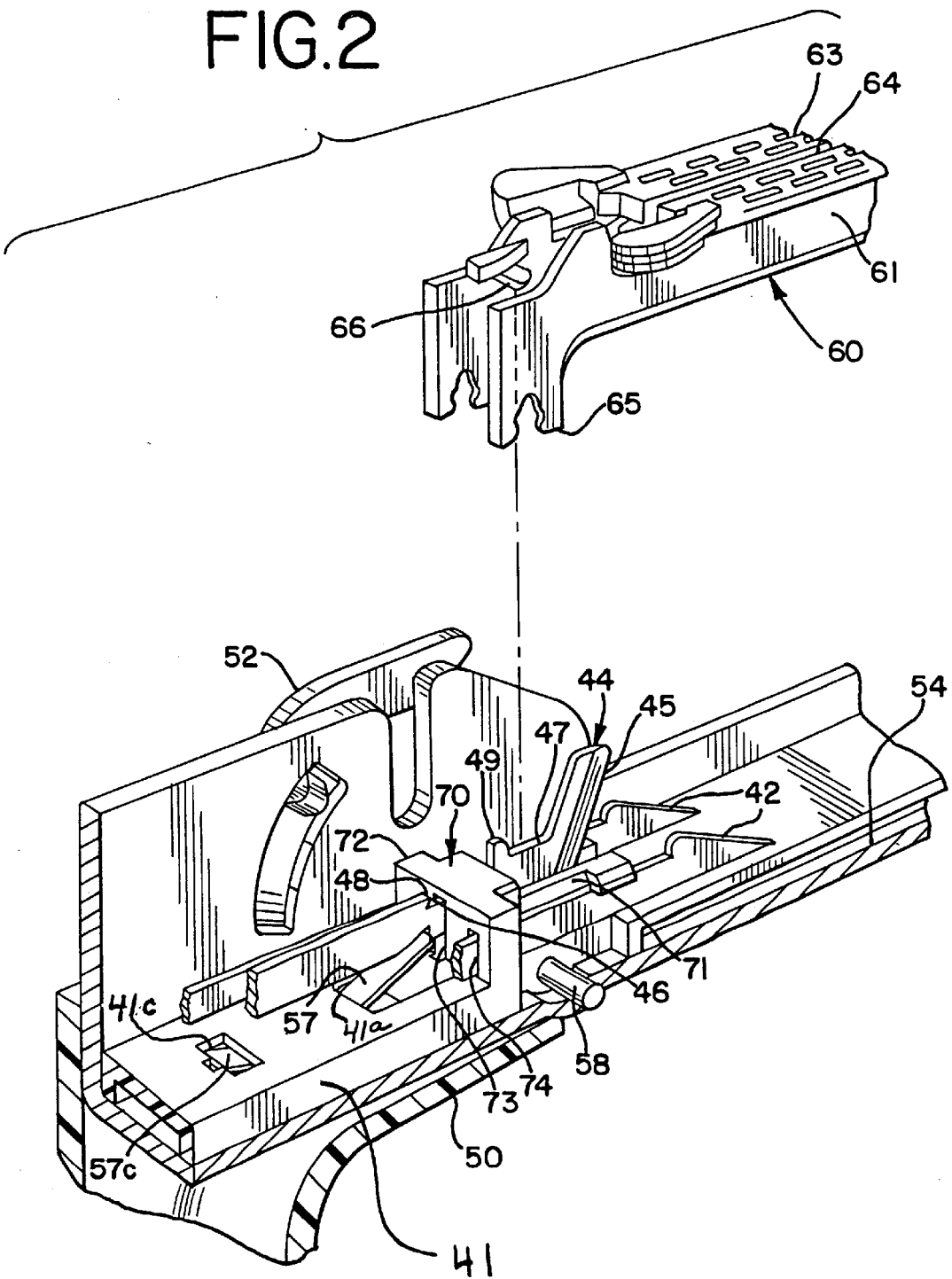
FIG. 2 is an exploded perspective view illustrating a locking mechanism, partially broken away, of the present surgical stapler.
Figure 3:
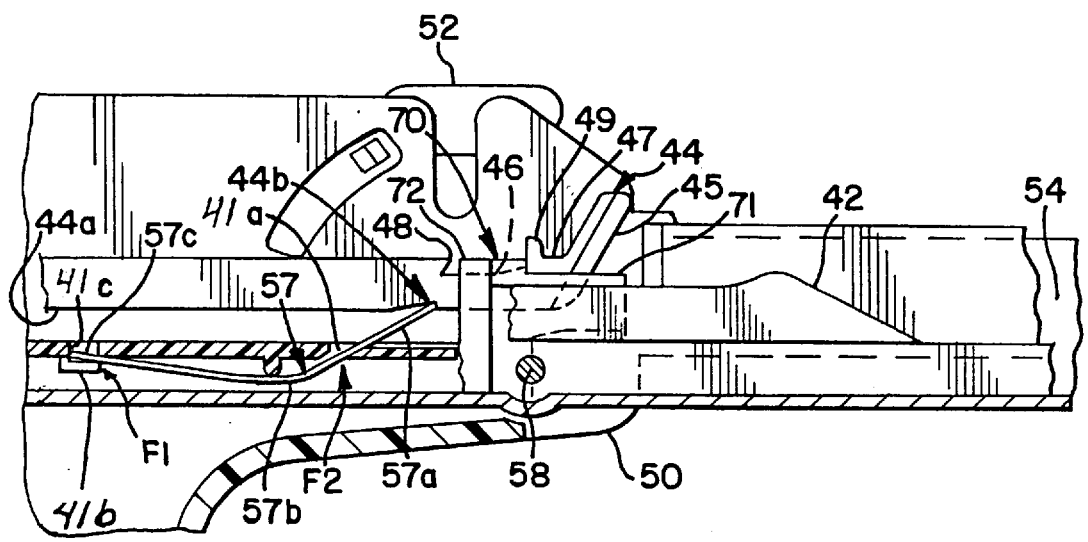
FIG. 3 is a side elevational view, in partial cross-section, illustrating the present surgical stapler prior to insertion of a staple cartridge therein, showing a cutting knife blade of the stapler in a locked, first position.

As shown in FIGS. 2 and 3, the spring 57 includes a spring finger 57a extending through a hole 54a of the spacer 41. The spring finger extends into an arcuate anchor portion 57b which is located beneath the spacer 41. The anchor portion terminates in an end tab 57c which is fixed to the spacer 41 by a clamp piece 41b beneath an aperture 41c. The clamp piece 41b presses the end tab 57c to an underside of the spacer 41. The clamp piece 41b at one end and the hole 41a at an opposite end of the arcuate anchor portion constitute the schematic fixing locations F1, F2 respectively as described in FIGS. 10a–10c.

Returning to FIG. 1, the lower handle portion 51 is pivotally movable between two positions. In a first open position of the lower handle portion 51, the handle portion extends at an angle with respect to lower jaw portion 53. In this position of the handle portion, a pair of C-shaped members 52 of the handle portion 51 are disengaged from a stationary locking pin 33 mounted on upper frame piece 30. In this position of the handle portion, the upper and lower frame pieces 30, 50 can be separated from each other, permitting insertion and removal of staple cartridge 60.

In the second, locking position of the lower handle portion 51, the C-shaped members 52 engage the locking pin 33, thus locking the upper and lower frame pieces 30 and 50 together. In this locking position, the movable handle portion 51 is positioned in generally parallel relationship to the lower jaw portion 53.

The firing or pusher assembly 40 comprises at least one pusher bar or firing wedge 42 (see FIG. 2), with the illustrated embodiment including two such firing wedges. A firing or actuation knob 59 (FIG. 1) is operatively joined to the firing assembly 40 by a pusher bar (not shown) for effecting longitudinal movement of the firing wedges 42 longitudinally along the spacer 41 and through the staple cartridge 60 when an unused staple cartridge has been positioned in lower jaw portion 53, and the upper and lower frame pieces 30, 50 secured to each other by locking engagement of C-shaped members 52 with locking pin 33.

Figure 4:
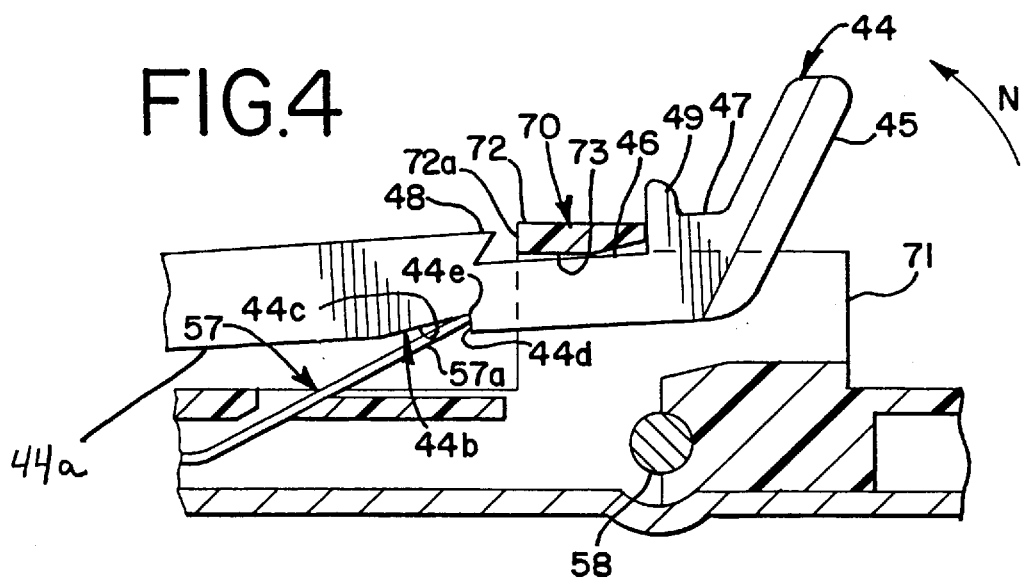
FIG. 4 is an enlarged detailed view in partial cross-section showing the locking mechanism locking the cutting knife blade in the first position thereof.

The locking mechanism of the present surgical stapler is intended to prevent use of the device unless the frame is fitted with an unused staple cartridge 60. The locking mechanism includes a block or roof member 70 (FIG. 2) formed on the spacer 41 and having a distally extending narrow roof portion 71 (FIGS. 3, 4). The roof portion 71 is integral with a widened roof portion 72 defining three slots. Knife slot 73 extends through the widened roof portion 72 and the narrow roof portion 71. The roof portion 72 defines two additional slots 74 through which firing wedges 42 respectively extend. The narrow roof portion 71 is positioned generally between the firing wedges 42. As firing wedges 42 slide through slots 74, knife blade 44 is movable distally through slot 73. The knife blade 44 includes a cutting surface 45, with the disposition of the knife blade between the illustrated firing wedges 42 configuring the present stapler for cutting of tissue while one or more rows of staples are simultaneously placed on each side of the cut tissue.

Not only is the knife blade 44 movable distally of the surgical stapler for effecting tissue cutting, the knife blade is also movable generally vertically between a first, locked position and a second, unlocked position thereof. In the first position of the knife blade assembly, illustrated in FIGS. 3 and 4, the knife blade assembly is out of alignment with knife slot 73 defined by roof member 70, thus preventing movement of the knife blade 44 through the roof member, and through an elongated knife slot 64 defined by the body of the staple cartridge 60.

Biasing leaf spring 57 ordinarily urges the knife blade 44 upwardly into this first, locked position. The leaf spring 57 includes the leaf spring finger 57a and the lower anchor portion 57b. The spring finger 57a is pressed against an underside 44a of the knife blade 44 and is received in a spring notch 44b of the blade 44. The notch 44b includes an inclined surface 44c which is angled downwardly, obliquely in the retraction direction R of the blade 44, and a contiguous stop surface 44d. The stop surface 44d is arranged substantially perpendicular to the retraction direction R.

Figure 5:
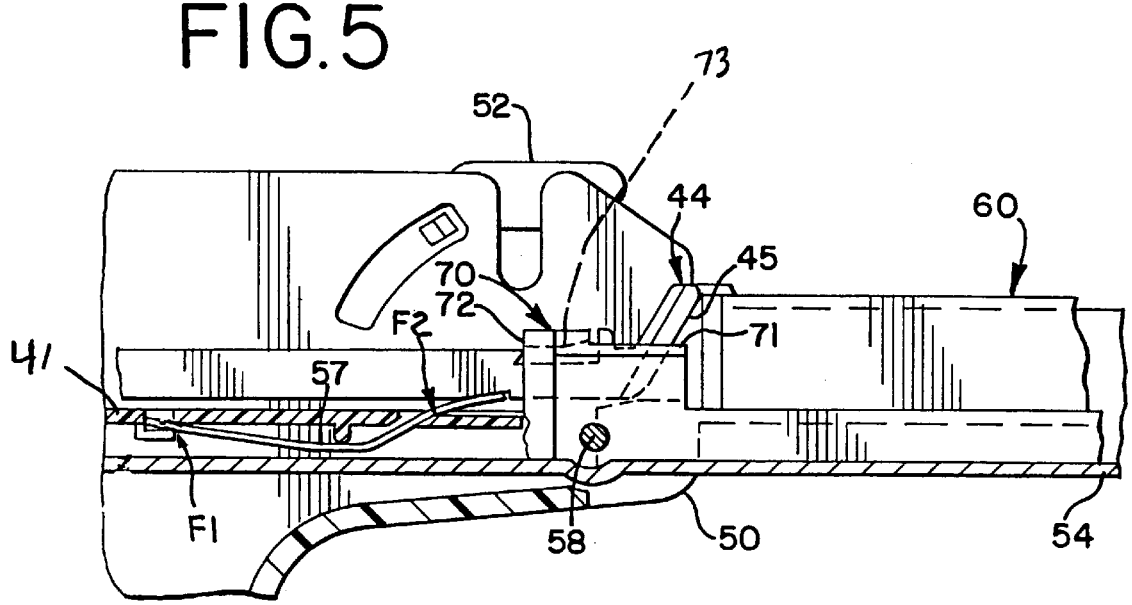
FIG. 5 is a view similar to that of FIG. 3 with a staple cartridge in place.

The knife blade 44 is movable vertically in opposition to the leaf spring 57 to a second, unlocked position of the knife blade. In this second position (FIGS. 5 and 6), the knife blade is positioned in alignment with knife slot 73, and is thus positioned for advancement distally through slot 73 in the roof member, and through knife slot 64 defined by staple cartridge 60.

Figure 6:
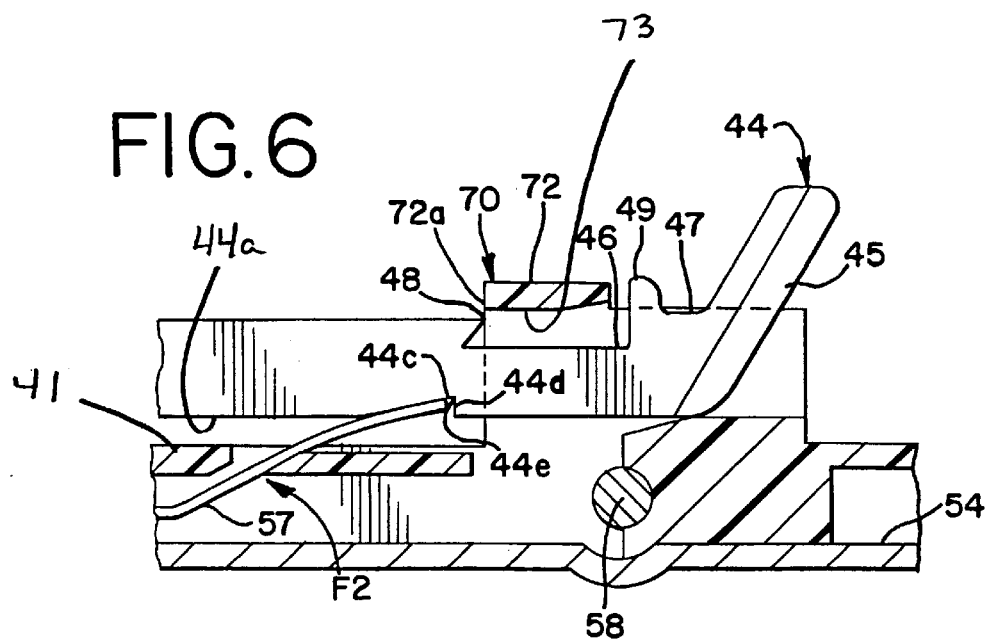
FIG. 6 is an enlarged detailed view in partial cross-section showing the cutting knife blade in a second, unlocked position thereof.
Figure 7:
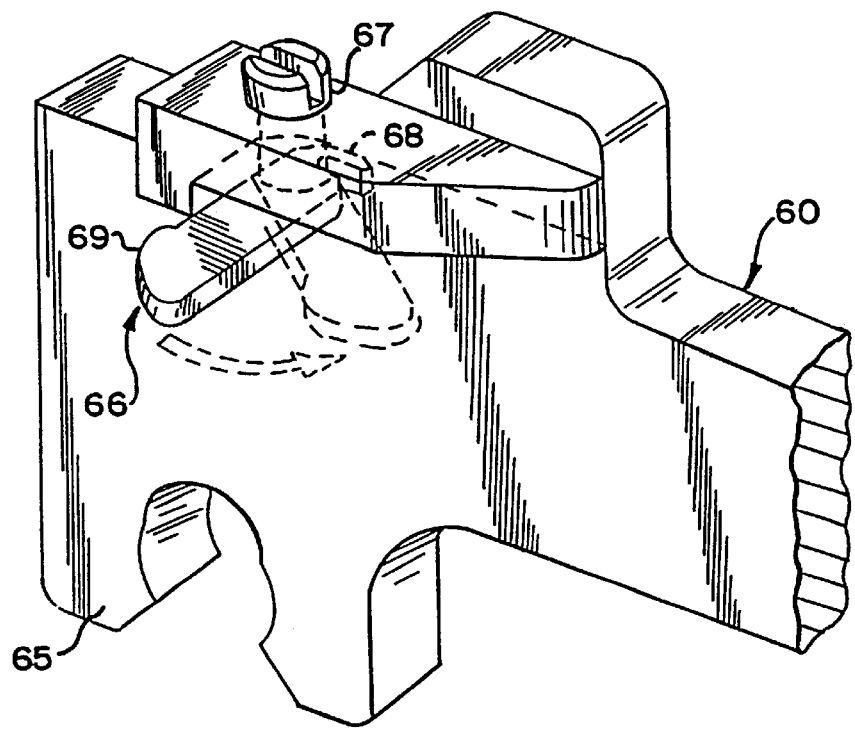
FIG. 7 is a fragmentary perspective view of a rotatable member of the locking mechanism of the present invention.

The specific cooperation of the knife blade 44 and the roof member 70 of the spacer 41 is best illustrated in FIGS. 4 and 6. As shown in FIG. 4, illustrating the first, locked position of the knife blade 44, leaf spring 57 pushes the knife blade up against roof member 70 of the spacer 41. Widened roof portion 72 of the spacer 41 engages a locking area 46 formed as a recess in the knife blade, with engagement of a locking portion 48 of the knife blade with the roof member 70 of the spacer 41, preventing distal movement of the knife blade through the roof member and through the elongated knife slot 64 of the staple cartridge. The locking portion 48 provides an exposed forward facing surface which abuts an exposed stationary stop surface 72a of the roof portion of the spacer 41. In this position of the knife blade, the firing wedges 44 of the firing assembly 40 are also substantially prevented from forward movement, since the knife blade and firing wedges (i.e., firing assembly 40) are generally movable in unison.

Movement of the knife blade 44 from its first position to its second, unlocked position, for advancement, is effected by disposition of an unused staple cartridge 60 in the channel 54 of lower jaw portion 53. The rotatable member 66, pivotably mounted by integral pin 67 on the body 61 of the staple cartridge 60, is engagable with the knife blade 44 at surface 47. As the staple cartridge is lowered into the lower jaw portion, the rotatable member 66 acts on the knife blade 44 in opposition to biasing leaf spring 57, thereby unlocking the knife blade by movement downwardly to its second position.

As will be observed in FIG. 6, wherein the knife blade 44 is illustrated in its second, unlocked position, locking portion 48 is moved from a position for engagement with roof member 70, to clear the surface 72a. The knife blade 44 is thus aligned with slot 73 to accommodate distal sliding movement of the knife blade. In this position of the knife blade, the knife blade and the firing wedges 42 are movable together distally of the stapler, thereby effecting sequential driving of staples 80 (via staple drivers 63; see FIG. 8) from the cartridge 60 as the cutting surface 45 of the knife blade effects tissue cutting by movement through the elongated knife slot 64 defined by the staple cartridge 60.

With particular reference to FIG. 7, and FIGS. 9a to 9d, features of the rotatable member 66 and its cooperation with the knife blade 44, are illustrated. As noted, the rotatable member 66 initially engages the knife blade 44, thereby urging the knife blade from its first to its second position, when the firing assembly 40 (including knife blade 44 and firing wedges 42) is in its retracted position. As the knife blade 44 is advanced distally of the stapler, upstanding portion 49 of the knife blade engages the rotatable member 66. This engagement acts to rotate the member 66 from its first position (FIG. 9a) to its second position (FIG. 9d), wherein the rotatable member is maintained in an out-of-the-way disposition with respect to the knife blade.

As the member 66 rotates, the member engages the body 61 of the staple cartridge 66 as the member moves to its second position. Such engagement is desirable since it acts to maintain the rotatable member in its second position after the knife blade has been advanced distally through the staple cartridge. However, such rotatable movement of member 66 is, of course, effected by the user of the stapler, and thus the force required for movement of the member from its first to its second position must be exerted by the user through the firing knob 59 and the firing assembly 40.

In order to reduce the "force to fire" exerted by the user of the stapler, the rotatable member 66 is configured to accommodate movement from its first to its second position. Specifically, the rotatable member 66 includes a resiliently flexible portion 68 which is yieldably engagable with the body of the staple cartridge as the rotatable member is moved from its first position to its second position. The flexible portion 68 is preferably provided in the form of a cantilevered arm positioned at a first end portion of the rotatable member. As will be observed, the rotatable member 66 is pivotally mounted on the cartridge body 61 at this first end portion. Engagement of the flexible portion 68 with the cartridge body is particularly illustrated in FIGS. 9b and 9c.

In order to assure movement of the rotatable member 66 to its second position, the rotatable member preferably comprises a cam projection 69 engagable by portion 49 of the knife blade 44 as the knife blade is advanced distally through the knife slot of the staple cartridge. Once the rotatable member has been moved to its second position, the free end portion of the cantilevered flexible portion 68 is positioned in generally confronting relationship with the cartridge body (see FIG. 9d). In this orientation of the flexible portion 68, the flexible member is positioned for engagement with the cartridge body so that movement of the rotatable member from its second position is substantially prevented. As will be appreciated, the cantilevered flexible portion extends from its base in a direction away from the direction of rotation of the member 66 about its pivot pin 67.

The free end of the pivot pin 67 can be bifurcated to render the pin resiliently compressible. The pin 67 can thus be compressed for insertion through the cartridge body 61, with the bifurcated portion of the pin 67 thereafter expanding outwardly to securely retain the rotatable member 66 on the cartridge body.

Upon retraction of firing assembly 40, including knife blade 44, the knife blade 44 returns to its locked position with respect to roof member 70. Rotatable member 66 remains in its second position, and thus does not engage portion 47 of the knife blade 44, with leaf spring 57 thus urging the knife blade upwardly with respect to the roof member of the spacer 41 so that locking portion 48 is positioned for engagement with the roof member. The handle 51 of the surgical stapler can be pivoted to unlock the upper and lower frame pieces of the stapler, thereby permitting separation of the frame pieces and removal of the used staple cartridge 60. Insertion of a fresh, unused staple cartridge 60 into the lower jaw portion 53 of the lower frame piece effects unlocking movement of the knife blade 44, by virtue of the rotatable member 66 of the unused cartridge being in the first position of the member 66. Engagement of the member 66 with the knife blade 44 at 47 moves the knife blade from its first, locked position to its second, unlocked position, with subsequent joining of the upper and lower frame pieces 30, 50, and locking of the frame pieces by movement of handle 51, thereafter preparing the stapler for reuse.

Figure 10A:
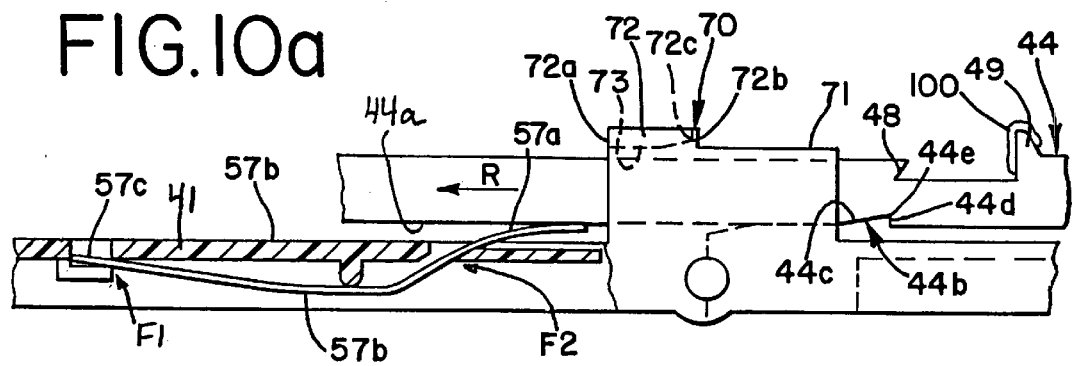
FIG. 10a is a schematic elevational view of the surgical stapler with the knife blade being retracted from a distal position to a proximal portion.

FIGS. 10a through 10d illustrate the improved locking mechanism of the present invention. As illustrated in FIG. 10a, it is possible for tissue material 100 to accumulate on the upstanding portion 49 of the knife blade 44, which when moved completely to the right in a retraction direction R can interfere with the movement of the locking portion 48 to pass through the slot 73 to clear the roof portion 72 of the spacer 41, to become engaged to a rear surface 72a of the roof portion 72 of the spacer 41. Additionally, due to repetitive contact with the upstanding member 49 and the roof portion 70, a crease or embedding can occur in a front surface 72b of the roof portion of the spacer 41 which can cause seizing of the upstanding member 49 at the crease 72c and a resulting decreased mobility of the knife blade in a vertical direction to engage the roof portion 72 of the spacer 41 with the locking portion 48. In this regard, the novel arrangement between the spring finger 57a and the spring notch 44a provides an upward and rearward thrust on the knife blade 44 to more efficiently press the upstanding member 49 through loose tissue 100 and engage the locking portion 48 to the roof portion 72 of the spacer 41.

The arrangement and angularity of the spring finger 57a and the oblique surface 44c causes a normal force K having an upward thrust component in the direction U and a rearward thrust component in the direction R on the knife blade 44 which in most cases is sufficient to lift the knife blade 44 such that the locking portion 48 engages the rear surface 72a of the roof portion of the spacer 41.

Figure 10B:
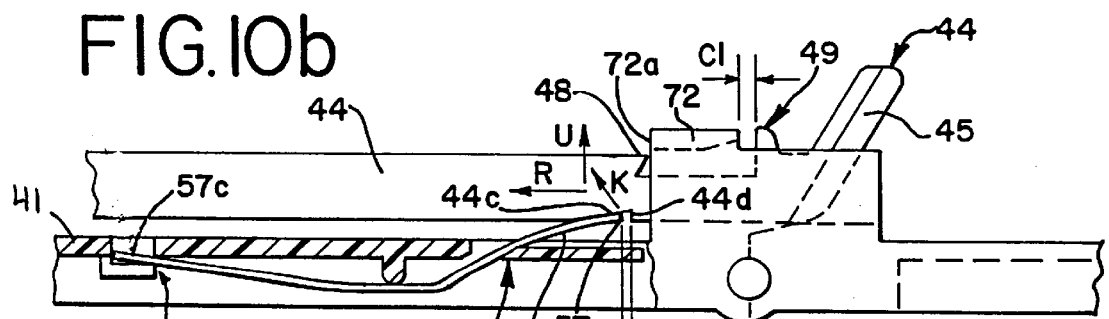
FIG. 10b is a schematic elevational view of the surgical stapler of FIG. 10a with the knife blade in a nearly fully retracted position.

FIG. 10b illustrates the knife blade 44 in a position sufficiently retracted to raise, but shown remaining in its second unlocked position. If the blade is somehow inhibited from raising, further retraction in the direction R results in a second action by the leaf spring 57. A clearance C1 between the upstanding member 49 and the roof portion 72 of the spacer 41 is greater than a clearance C2 between an end 57c and the stop surface 44d. Thus, as the blade 44 is further retracted, the stop surface 44d makes contact with the free end 57c.

Figure 10C:
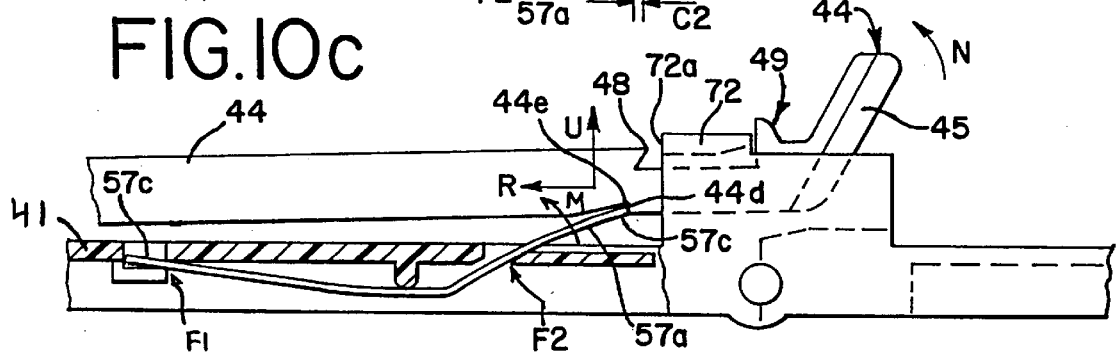
FIGS. 10c and 10d are a schematic elevational view of the surgical stapler of FIG. 10a with the knife blade in a fully retracted and locked position.
Figure 10D:
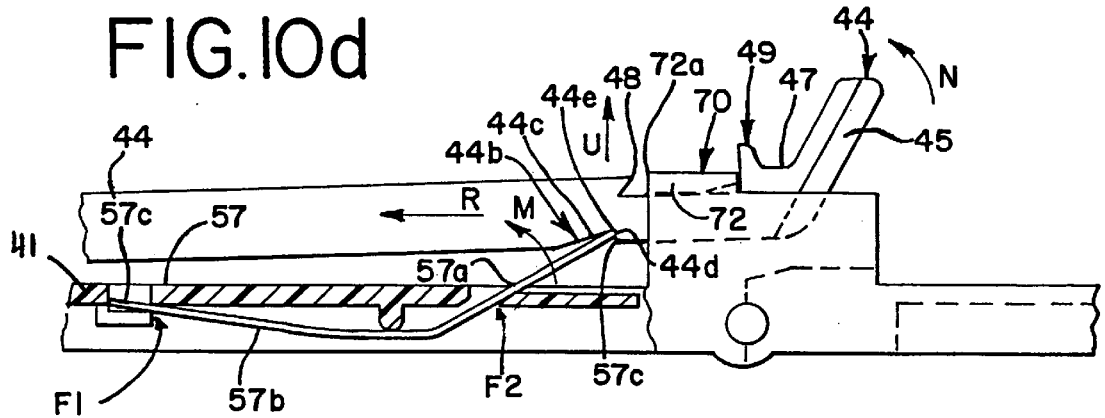

As illustrated in FIG. 10c, further progression of the blade 44 in a retraction direction R drives the spring finger 57a into an inside corner 44e formed between the inclined surface 44c and the stop surface 44d. At this point, further retraction of the blade 44 in the direction R forces a swing motion or rotary motion M of the spring finger 57a and the blade 44. Because of the relative stiffness of the spring 57 and its clamped connection at fixing location F1 and pressed abutment at fixing location F2, the motion of the spring finger 57a is a swinging movement about an axis of flexing located at F2. In effect, the spring finger between the corner 44e and the location F2 acts as a linkage member pinned at both ends, and "thrusts" the knife blade upwardly during retraction in a pivoting and sliding movement N, by pivoting movement of the spring finger 57a. The blade 44 achieves its fully retracted and locked position as shown in FIG. 10d. Thus, during this last action by the spring finger 57a, the spring finger acts substantially as a structural member pinned at 44e and F2 and under compression to mechanically elevate the knife blade, rather than merely acting as a flexing cantilever leaf spring resiliently urging the knife blade upwardly.

The action of the spring 57 and the notch 44a ensures an effective engagement of the locking portion 48 to the rear surface 72a. In addition, the thrust feature clears out any tissue accumulation, enhancing ability of the knife to restore to its full elevated return position.

From the foregoing, it will be observed that numerous modifications and variations can be effected without departing from the true spirit and scope of the novel concept of the present invention. It is to be understood that no limitation with respect to the specific embodiment illustrated herein is intended or should be inferred. The disclosure is intended to cover all such modifications as fall within the scope of the appended claims.

What is claimed:

1. A surgical stapler comprising:
   a frame;
   a leaf spring carried by said frame, said leaf spring having a spring finger;
   a staple cartridge positionable in said frame and comprising a cartridge body containing at least one row of staples, said cartridge defining an elongated knife slot;
   at least one firing wedge carried by said frame for movement longitudinally of said staple cartridge for effecting sequential driving of said staples from said cartridge; and
   a knife blade carried by said frame for movement longitudinally of said staple cartridge through said elongated knife slot, said knife blade being movable between a first position wherein said knife blade is substantially prevented from moving through said knife slot, and a second position wherein said knife blade is movable through said knife slot, said leaf spring arranged to urge said knife blade toward said first position, said knife blade having a spring stop surface formed on a first side of said knife blade facing said leaf spring, said stop surface facing toward a retraction direction of said knife blade, said spring finger inclined from said frame toward said knife blade and pivotable at said frame, said spring finger having a free end engagable by said stop surface, said spring finger pivoted by retraction of said blade, said blade elevated by pivoting of said spring finger.

2. A surgical stapler in accordance with claim 1, wherein said blade includes a spring notch, and said stop surface is formed as a transverse surface of said spring notch, said spring notch further including an oblique surface contiguous to said stop surface and forming a corner therewith.

3. A surgical stapler in accordance with claim 1, wherein said frame comprises a stationary blade stop surface facing in a retraction direction and adjacent said knife blade, and said knife blade includes a locking portion facing away from the retraction direction and arranged to abut said stationary stop surface in said first position.

4. A surgical stapler in accordance with claim 3, wherein said locking portion comprises a forward facing surface of a recess into a second side of said knife blade opposite said first side.

5. A surgical stapler in accordance with claim 4, wherein said frame comprises a stationary block having a knife slot therethrough for allowing reciprocation of said knife blade and having a roof portion overlying said knife blade within said knife slot, said stationary blade stop surface formed on a rear surface of said roof portion.

6. A surgical stapler, comprising:
   a frame having a stationary block which includes a roof member and a knife slot, said roof member overlying said knife slot and having a front surface and a rear surface facing opposite directions along a longitudinal direction;
   a leaf spring anchored to said frame having a spring finger extending upwardly from said frame;
   a knife blade movable longitudinal through said knife slot beneath said roof member and slidable on said spring finger, said knife blade having a cutting surface on a distal end thereof and having a locking portion spaced from said cutting surface along said blade, said leaf spring urging said locking portion to front said rear surface of said roof member when in a first position to prevent forward longitudinal movement of said blade;

said blade having a spring notch on a bottom side thereof, said spring notch having an oblique surface angled downwardly in a retraction direction, and a spring stop surface contiguous with said oblique surface and substantially perpendicular to the longitudinal direction, during retraction said spring finger engagable into said spring notch, slidable along said oblique surface and abutting said stop surface.

7. A stapler in accordance with claim 6, wherein said leaf spring includes a base portion anchored to said frame, and spring finger is declined from a free end thereof to said base portion.

8. A surgical stapler for simultaneous cutting and stapling, comprising:

a frame including an upper frame portion and a lower frame portion, said frame adapted to hold a removable staple cartridge;

a pusher assembly carried by said lower frame portion, said pusher assembly having a firing wedge for sequentially deploying staples from the staple cartridge as the firing wedge progresses from a proximal position to a distal position;

a blade carried by said lower frame portion and movable with said firing wedge from a proximal position to a distal position, said blade having an elongate body arranged lengthwise along said direction of movement and a cutting surface arranged angled from said elongate body and extending from said lower frame portion toward said upper frame portion;

said elongate body having a top surface with a locking portion having a first exposed surface facing toward said distal position, and a lower surface having a longitudinal guiding edge for guiding vertical position of said elongate body from said proximal position to said distal position wherein said guiding edge includes an oblique surface adjacent said proximal position, and a spring stop surface formed as a notch adjacent said oblique surface;

said lower frame portion including a stationary roof portion located at said proximal position and having a slot for guiding said elongate body and a second exposed surface facing away from said distal position, wherein said elongate body is movable vertically in the proximal position to position said first exposed surface of said top surface of said elongate body to abut said second exposed surface of said roof portion to prevent movement of said elongate body toward said distal position; and a leaf spring carried by said lower frame portion and arranged beneath said lower surface of said elongate body and having a spring finger urged against said guiding edge;

said spring finger interacting with said oblique surface of said guiding surface to urge said elongate body upward and backward away from said distal position and abutting said spring stop surface to allows said spring finger to pivot upwardly and elevate said knife blade to position said first exposed surface to abut said second exposed surface.

9. The surgical stapler according to claim 8, wherein said leaf spring includes an arcuate anchor portion connected to said spring finger, said anchor portion anchored at one end to said lower frame portion and pressed at an opposite end by said lower frame piece.

10. The surgical stapler according to claim 9 wherein said spring finger is inclined substantially parallel to said oblique region.

11. A stapler according to claim 8, wherein said stop surface is formed by a triangular notch formed into said lower surface of said elongate body.

12. The surgical stapler in accordance with claim 11, wherein said first exposed surface of said locking portion is formed by a recess formed into said top surface of said elongate body.

13. The surgical stapler in accordance with claim 8 further comprising an unlock mechanism activatable by the installation of a new staple cartridge to overcome the urging of said leaf spring to deflect said first exposed surface of said locking portion out of registry with said second exposed surface of said stationary roof portion.

14. The surgical stapler in accordance with claim 5 wherein said frame comprises a spacer, said spacer having an elongate body formed integrally with said stationary block, and a lower frame piece having a channel for receiving said spacer.

15. The surgical stapler in accordance with claim 6 wherein said frame comprises a spacer, said spacer having an elongate body formed integrally with said stationary block, and a lower frame piece having a channel for receiving said spacer.

16. The surgical stapler in accordance with claim 8 wherein said lower frame portion comprises a spacer, said spacer having an elongate body formed integrally with said stationary roof portion and a lower frame piece having a channel for receiving said spacer.

\* \* \* \* \*